United States Patent
Bote Bote

(10) Patent No.: US 7,361,306 B2
(45) Date of Patent: Apr. 22, 2008

(54) DEVICE AND METHOD FOR MEASURING COAGULATION TIME AND PLATELET ACTIVITY

(76) Inventor: Antonio Bote Bote, Carrera No. 4, 1roC, Mostoles, Madrid (ES) E 28931

( * ) Notice: Subject to any disclaimer, the term of this patent is extended or adjusted under 35 U.S.C. 154(b) by 409 days.

(21) Appl. No.: 10/512,294

(22) PCT Filed: Apr. 15, 2003

(86) PCT No.: PCT/ES03/00174

§ 371 (c)(1),
(2), (4) Date: Oct. 15, 2004

(87) PCT Pub. No.: WO03/087817

PCT Pub. Date: Oct. 23, 2003

(65) Prior Publication Data

US 2005/0180886 A1    Aug. 18, 2005

(30) Foreign Application Priority Data

Apr. 18, 2002 (ES) ................................ 200200904

(51) Int. Cl.
*G01N 33/86* (2006.01)
(52) U.S. Cl. .......................... 422/73; 422/68.1; 422/72; 436/45; 436/63; 436/69; 435/2; 435/13; 600/369; 73/64.41

(58) Field of Classification Search ................ 436/43, 436/45, 63, 69, 174; 422/63, 64, 67, 68.1, 422/72, 73; 435/2, 13; 600/369; 73/64.41
See application file for complete search history.

(56) References Cited

U.S. PATENT DOCUMENTS

| | | | |
|---|---|---|---|
| 3,861,197 A * | 1/1975 | Adler | 73/54.31 |
| 4,081,242 A * | 3/1978 | Girolami | 73/54.01 |
| 4,612,801 A * | 9/1986 | Girolami | 73/64.41 |
| 5,072,610 A * | 12/1991 | Martinoli et al. | 73/53.01 |
| 5,181,415 A * | 1/1993 | Esvan et al. | 73/54.28 |
| 5,777,215 A * | 7/1998 | Calatzis et al. | 73/64.41 |
| 6,711,943 B1 * | 3/2004 | Schob | 73/54.28 |
| 2003/0180824 A1 * | 9/2003 | Mpock et al. | 435/13 |
| 2004/0131500 A1 * | 7/2004 | Chow | 422/72 |

\* cited by examiner

Primary Examiner—Maureen M. Wallenhorst
(74) Attorney, Agent, or Firm—Sanchelima & Assoc., P.A.

(57) ABSTRACT

The present invention refers to a novel device for measuring coagulation time and platelet activity wherein the patient can measure his or her coagulation time and platelet activity without the aid of medical professionals due to the fact that this device is fully autonomous. A blood sample (14) is deposited in the dish (3) and reacted with a reactant (16). The display (9) then shows the coagulation time and platelet activity of the patient.

6 Claims, 1 Drawing Sheet

DEVICE AND METHOD FOR MEASURING COAGULATION TIME AND PLATELET ACTIVITY

OBJECT OF THE INVENTION

The present invention refers to a novel device for measuring coagulation time and platelet activity and to a process thereof, whereby, thanks to this electromechanically-operated, small-sized and battery-powered device, a patient can measure his or her coagulation time and platelet activity without the aid of medical professionals, furthermore being able to be connected to the medical center responsible for the patient clinical follow-up by means of telephone, Internet network or any other communication means.

BACKGROUND OF THE INVENTION

The traditional method regarding measuring coagulation time and platelet activity of a patient hitherto has consisted of the analysis of these parameters in a clinical laboratory, by means of using instruments situated in clinical analysis laboratories, which implies frequent trips for patients, with the resulting social and financial damage for them, as well as for public health institutions, in addition to usually not being carried out with the periodicity recommended by medical specialists.

All the drawbacks mentioned above are emphasized when the measurement of coagulation time and platelet activity is carried out on a patient with cardiovascular diseases, given that these patients are treated with anticoagulant products with personalized doses for each patient.

These doses depend to a large extent on the blood characteristics of each patient, the two most important ones being those characterized by the parameters called "coagulation time" and "platelet activity", therefore they must periodically come to a clinical analysis laboratory to carry out the corresponding analyses in order to measure said parameters.

DESCRIPTION OF THE INVENTION

With the device for measuring coagulation time and platelet activity and process thereof, object of the present invention, all the drawbacks mentioned above are intended to be palliated or improved to which end it is a measuring process by means of using a device in which a blood drop of the patient is introduced, such that this blood falls in the device, reacting with a reactant which is incorporated in the device whereby a change of the blood state is achieved and, thanks to this change, the coagulation time and platelet activity can be measured. To that end, it is a device that includes a frustoconical-shaped cup inside of which a likewise frustoconical-shaped rotor rotates, with the same taper but of a slightly smaller diameter. The blood with the reactant is placed in the gaps between the rotor and the cup, the reactant serving as the coagulation precursor whereby a clot is formed in the gap, causing a decrease of the rotating speed of the rotor. This speed decrease is measured by a speed sensor and interpreted by an electronic circuit, resulting in the measurement of the coagulation time and/or platelet activity.

The operation of this device is prepared by using batteries, which provides this device with an obvious autonomy.

DESCRIPTION OF THE DRAWINGS

To complement the description being made and for the purpose of helping to better understand the features of the invention, a series of drawings is attached to the present specification as an integral part thereof, in which with an illustrative and non-limiting character, the following has been shown.

PREFERRED EMBODIMENT OF THE INVENTION

Figure 1:
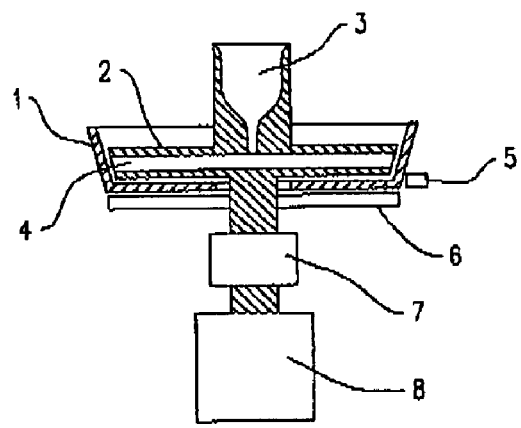
FIG. 1 shows a schematic view of the process for obtaining the measurement of the "coagulation time" and "platelet activity" parameters.
Figure 2:
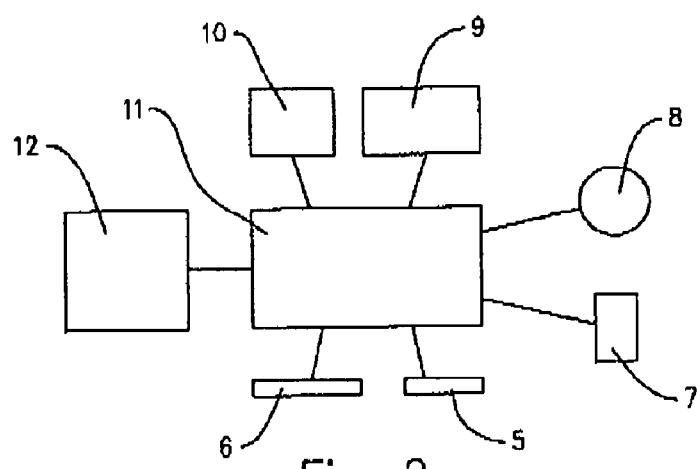
FIG. 2 shows a view of mechanical operating of the invention.
Figure 3:
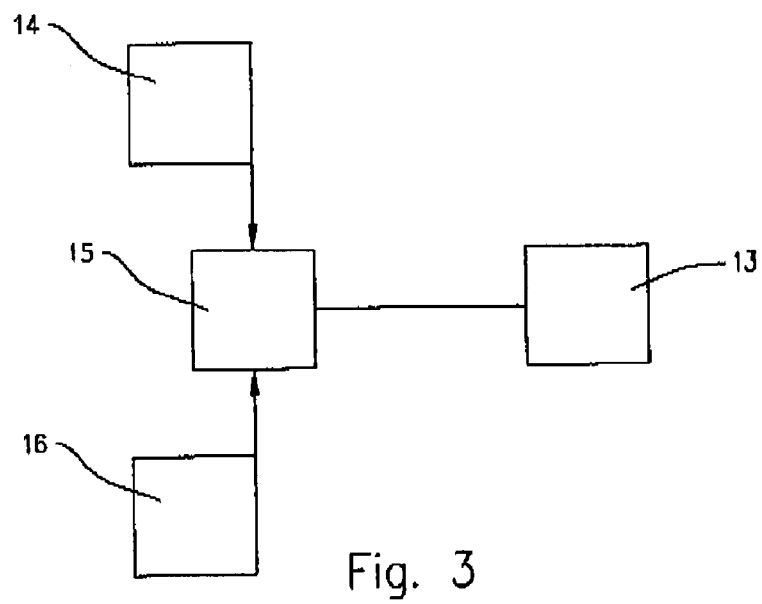
FIG. 3 shows a view of the interconnection of the components.

As can be seen in the figures, a blood sample (14) placed in the dish (3), which is connected with the diametrical conduit (4), which has the reactant (16), is distinguished in the first place. This blood sample (14) together with the reactant (16) is ejected to the gap generated between the cup (1) and the rotor (2), thanks to the aid of the centrifugal force generated 25 by the circular motion of the rotor (2) rotating due to the action of the electric motor (8), a speed sensor (7) is used for measuring the speed decrease of the rotor (2) caused by clot (15) resulting from the mixing of the blood sample (14) and reactant (16);. Heating element (6) is used for maintaining the assembly at a temperature between 35 and 40 degrees centigrade and its corresponding temperature sensor (5) is used for assuring this temperature range is kept.

In one of the prepared embodiments, measuring device (13) is implemented with a small frustoconical or cylindrical-shaped cup (1), inside of which a likewise frustoconical-shaped rotor (2) coaxially rotates. Rotor (2) has the same taper and slightly smaller diameter, such that there is a small clearance between them and there is no friction between their respective side walls nor between their bases.

Blood sample (14) of a patient and reactant (16) functioning as a coagulation activator, are placed in the gaps between interior rotor (2) and cup (1). The reactant (16) to be used will depend on whether the "coagulation dire" or "platelet activity" is to be measured.

Due to the rotation of the rotor (2), both products are thoroughly mixed, a biochemical process which, after a certain time, gives rise to die clot (15) formation being initiated, causing an increase of mechanical friction between the rotor (2) and the cup (1) detected due to its effect on the speed and on the torque of the cylinder.

In the event that the coagulation time is being measured, friction will suddenly increase in the moment in which clot (15) is produced. The time elapsed between the start of the process and the moment in which the friction increase occurs is measured by a control circuit (11), and with the due corrections automatically carried out, the so called "coagulation time" is obtained.

If "platelet activity" is being measured, the friction increase will be progressive in accordance with clot (15) formation and the manner in which it varies will be analyzed by the control circuit (11) to measure said parameter.

Given that the entire process must be carried out in a temperature range of 35 to 40° C., a heating element (6) and a temperature sensor (5) are incorporated under the cup (1). The control circuit (11) is in charge of maintaining the cup (1) and the rotor (2) at said temperature and of notifying the patient by the display (9) that the measuring device (13) is ready to be used once said temperature is reached and stabilized.

For the purpose of facilitating the dosage of the reactant (16) and of the patient blood sample (14), the rotor (2) has a diametrical conduit (4) in which the reactant (16) is housed.

For the purpose of facilitating the placing and subsequent dosage of the patient blood sample (14), the rotor (2) has a small dish (3) in the center of the upper face, which is connected at its lower portion with the center of the diametrical conduit (4) containing the reactant (16).

Once the measuring device (13) is on, and the time necessary to reach the operating temperature has elapsed, which is indicated to the patient by means of a small display (9), the patient will place a blood sample (14), obtained by a finger puncture, for examples in dish (3) intended for that purpose. The patient will then indicate to the measuring device (13) by means of the keyboard (10) that the measuring process can begin.

Said process begins with the phase of ejecting the reactant (16) and the blood sample (14) required for the clot (15) formation to occur. For that purpose, the rotor (2) is subjected to a very high rotating speed by means of an electric motor (8), the rotating shaft of which is solidly attached thereto, whereby, due to the centrifugal force, the reactant (16) will be ejected to the gap existing between the rotor and the cup.

Due to the vacuum generated in the diametrical conduit (4) of the rotor (2) due to the ejection of the reactant (16) contained therein, the blood sample (14), previously placed in the dish (3) located in the upper portion of the rotor (2), is also ejected towards said gap where, aided by the rotating motion, it is mixed with the reactant (16), the coagulation process itself beginning in that moment.

The amount of the ejected blood sample (14) will depend on the rotating speed of the rotor (2) and on the time the latter is rotating at high speed. Both parameters are controlled by the control circuit (11).

Once the reactant (16) and the blood sample (14) are ejected, the rotor (2) begins to rotate at a very slow speed. In this phase of the process, the control circuit (11) is in charge of measuring and controlling the speed and torque of the motor solidly attached to the rotor (2) by means of the speed sensor (7). The increases in the braking torque or decreases of the speed will indicate that coagulation is taking place. A calculation, carried out by the control circuit (11) from said variations according to the time, will serve for measuring the parameter object of the analysis.

The control circuit (11) is configured as a device provided with the electronic and electric components necessary for providing the necessary energy to the heating element (6) once the user activates the cycle start order by means of the keyboard (10), until the temperature sensor (5) indicates to the user that the suitable temperature has been reached, at which time the patient will be notified by means of the display (9) that he or she can place the blood sample (14) in the dish (3).

The control circuit (11) is configured as a device provided with the electronic and electric components and automatisms necessary for providing the necessary power to the electric motor (8) by means of the power supply unit (12) once the patient has placed the blood sample (14) in the dish (3), such that the rotor (2) rotates at the required speed and for the necessary time to eject the reactant (16) contained in the diametrical conduit (4) of the rotor (2) due to the effect of centrifugal force, as well as the blood sample (14) placed in the dish (3), due to the effect of the vacuum generated due to the ejection of the reactant and likewise to the centrifugal force. circuit (11) includes the electronic and electric components for providing the necessary power to the electric motor (8) by means of power supply unit (12) so that the motor rotates at a certain speed once the ejection cycle of the reactant (16) contained in the diametrical conduit (4), and of the blood sample (14) previously placed in the dish (3), has concluded.

Control circuit (11) is configured as a device provided with the necessary electronic and electric components for measuring at all times the rotating speed during the rotating phase of rotor (2), from speed sensor element (7) connected thereto, as well as the braking torque exerted by the clot (15) formation located in the gap existing between The rotor (2) and the cup (1) by measuring the current consumption of the motor (8).

The control circuit (11) is configured as a device provided with the necessary electronic and electric components to carry out the necessary calculations from the rotating speed and braking torque values obtained according to what is indicated in the previous paragraph, designed for obtaining the parameters called "coagulation time" or "platelet activity" as appropriate.

Having sufficiently described the nature of the present invention, as well as a manner of taking it to practice, all that remains is to add that it is possible to introduce changes in shape, materials and arrangement in the invention as a whole and in parts making it up, as long as said changes do not substantially change the features of the invention which are claimed below:

The invention claimed is:

1. A device for measuring the coagulation time and platelet activity in a blood sample, comprising:
    A) electric motor means for providing a rotational movement, said motor means further including means for sensing and controlling the speed of said rotational movement, which is proportional to the current drawn from an electric power source;
    B) rotor means having a substantially frustoconical shape, said rotor means being coupled to said motor means for receiving said rotational movement;
    C) a stationary frustoconical cup member coaxially housing said rotor means so that a surface gap is defined between said rotor means and said cup member;
    D) container means disposed within the rotor means for receiving a predetermined amount of a blood sample and coagulation reactant, wherein said container means includes conduit means with at least one transversal outlet cooperatively disposed to deposit a predetermined amount of said blood sample and reactant in said gap;
    E) control circuit means for measuring the changes of said rotational movement over predetermined periods of time to determine frictional forces related to the clotting of said sample of blood and reactant in said gap; and
    F) means for controlling and keeping the temperature of said device over a predetermined range.

2. The device set forth in claim 1 further including:
    G) means for measuring the current drawn by said motor means and being connected to said control circuit means so that said current drawn is sensed over predetermined periods of time that are correlated with the platelet activity of said blood sample.

3. The device set forth in claim 2 wherein said motor means includes a rotating shaft and said cup member includes a cooperative through opening that permits said shaft to go through.

4. The device set forth in claim 3 wherein said conduit means holds said coagulation reactant.

5. The device set forth in claim 4 wherein said means for controlling and keeping the temperature of said device keeps the temperature between 35° C. and 40° C.

6. The device set forth in claim 5 wherein said blood sample and coagulation reactant are deposited in said gap with the aid of centrifugal forces.

* * * * *